United States Patent
Gaur

(10) Patent No.: US 6,764,987 B1
(45) Date of Patent: Jul. 20, 2004

(54) GUM AND DENTURE ADHESIVE CLEANER COMPRISING ALUM

(76) Inventor: Hira Gaur, 11401 Gaviots Ave., Granada Hills, CA (US) 91344

( * ) Notice: Subject to any disclaimer, the term of this patent is extended or adjusted under 35 U.S.C. 154(b) by 0 days.

(21) Appl. No.: 10/387,694

(22) Filed: Mar. 12, 2003

Related U.S. Application Data

(60) Provisional application No. 60/363,260, filed on Mar. 12, 2002.
(51) Int. Cl.$^7$ .................................................. A61K 7/16
(52) U.S. Cl. ............................ 510/116; 424/49; 424/52
(58) Field of Search ................................ 510/116, 492, 510/467; 424/49, 52, 57

(56) References Cited

U.S. PATENT DOCUMENTS

| | | | |
|---|---|---|---|
| 4,374,824 A | * | 2/1983 | Wahmi .......................... 424/58 |
| 5,261,817 A | | 11/1993 | Nack |
| 5,543,443 A | | 8/1996 | Rajaiah et al. |
| 5,747,008 A | * | 5/1998 | Wason et al. .................. 424/52 |
| 6,124,374 A | | 9/2000 | Kolias et al. |

\* cited by examiner

*Primary Examiner*—Necholus Ogden
(74) *Attorney, Agent, or Firm*—Matthew J. Peirce

(57) ABSTRACT

A chemical composition for cleaning an individual's dentures and gums is disclosed. The chemical composition would be in powder form but instead could be made into liquid form by adding water. The chemical composition would brushed onto dentures in an effort to clean the dentures of any powder or substance on them that remains to them after a person has removed them from their mouth.

6 Claims, No Drawings

GUM AND DENTURE ADHESIVE CLEANER COMPRISING ALUM

This application claims the benefit of provisional application No. 60/363,260, filed Mar. 12, 2002.

I. BACKGROUND OF THE INVENTION

The present invention concerns that of a new and improved chemical composition for cleaning an individual's dentures and gums.

II. DESCRIPTION OF THE PRIOR ART

U.S. Pat. No. 6,124,374, issued to Kolias, discloses a denture adhesive and cleaning composition.

U.S. Pat. No. 5,543,443, issued to Rajaiah, discloses a denture adhesive composition which provides for easy removal.

U.S. Pat. No. 5,261,817, issued to Nack, discloses a denture adhesive removing tool.

III. SUMMARY OF THE INVENTION

The present invention concerns that of a new and improved chemical composition for cleaning an individual's dentures and gums. The chemical composition would be in powder form but instead could be made into liquid form by adding water. The chemical composition would brushed onto dentures in an effort to clean the dentures of any powder or substance on them that remains to them after a person has removed them from their mouth.

There has thus been outlined, rather broadly, the more important features of a denture and gum cleaner that the detailed description thereof that follows may be better understood and in order that the present contribution to the art may be better appreciated. There are, of course, additional features of the denture and gum cleaner that will be described hereinafter and which will form the subject matter of the claims appended hereto.

In this respect, before explaining at least one embodiment of the denture and gum cleaner in detail, it is to be understood that the denture and gum cleaner is not limited in its application to the details of construction and to the arrangements of the components set forth in the following description or illustrated in the drawings. The denture and gum cleaner is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present denture and gum cleaner. It is important, therefore, that the claims be regarded as including such equivalent constructions insofar as they do not depart from the spirit and scope of the present invention.

It is therefore an object of the present invention to provide a denture and gum cleaner which has all of the advantages of the prior art and none of the disadvantages.

It is another object of the present invention to provide a denture and gum cleaner which may be easily and efficiently manufactured and marketed.

It is another object of the present invention to provide a denture and gum cleaner which is of durable and reliable construction.

It is yet another object of the present invention to provide a denture and gum cleaner which is economically affordable and available for relevant purchasing government entities.

Other objects, features and advantages of the present invention will become more readily apparent from the following detailed description of the preferred embodiment when considered with the attached drawings and appended claims.

IV. DESCRIPTION OF THE PREFERRED EMBODIMENT

Priority is hereby claimed to application Ser. No. 60/363, 260, filed on Mar. 12, 2002.

The present invention concerns that of a new and improved chemical composition for cleaning an individual's dentures and gums. The chemical composition would be in powder form but instead could be made into liquid form by adding water. The chemical composition would brushed onto dentures in an effort to clean the dentures of any powder or substance on them that remains to them after a person has removed them from their mouth.

The chemical composition would preferably comprise the following substances and ratios:

1 parts alum, commonly known as potassium aluminum sulfate 4 parts water.

The alum would be dissolved in the water to the extent it could be, and then the chemical composition would be used in conjunction with a toothbrush or other type of cleaning device on a pair of dentures to remove of any powder or substance on them that remains to them after a person has removed them from their mouth.

The parts of the chemical composition would preferably be measured on a weight/weight basis, due to the fact that the "volume" of alum could not be accurately measured. The chemical formula for alum is $K_2SO_4.Al_2(SO_4)_3.24H_2O$.

In addition to the ingredients listed in the above composition, a flavoring could be added. Some types of flavorings available would be peppermint, spearmint, fruit, or other commonly used flavors in candies, mints, and gums on the market today.

What I claim as my invention is:

1. A chemical composition for cleaning an individual's dentures and gums, the chemical composition comprising:
   (a) one part alum, and
   (b) four parts water.

2. A chemical composition for cleaning an individual's dentures and gums according to claim 1 wherein the components in the chemical composition are measured on a weight/weight basis.

3. A chemical composition for cleaning an individual's dentures and gums according to claim 2 wherein the chemical composition further comprises flavoring.

4. A chemical composition for cleaning an individual's dentures and gums according to claim 3 wherein the flavoring is a peppermint flavoring.

5. A chemical composition for cleaning an individual's dentures and gums according to claim 3 wherein the flavoring is a spearmint flavoring.

6. A chemical composition for cleaning an individual's dentures and gums according to claim 3 wherein the flavoring is a fruit flavoring.

* * * * *